United States Patent [19]
Kini et al.

[11] Patent Number: 6,075,129
[45] Date of Patent: Jun. 13, 2000

[54] PROTEIN MOLECULES AND USES THEREFOR

[75] Inventors: Manjunatha R. Kini; Sivan Subburaju; Geraldine Lye Seem Chow, all of Singapore, Singapore

[73] Assignee: National University of Singapore, Singapore

[21] Appl. No.: 09/090,602

[22] Filed: Jun. 4, 1998

[30] Foreign Application Priority Data

Jan. 6, 1998 [SG] Singapore ............................ 9800055-7

[51] Int. Cl.[7] ................................................. A61K 38/00
[52] U.S. Cl. ............................ 530/856; 514/21; 514/822
[58] Field of Search ............................ 530/856; 514/21, 514/822

[56] References Cited

U.S. PATENT DOCUMENTS

| | | | |
|---|---|---|---|
| 4,016,043 | 4/1977 | Schuurs et al. | 195/103.5 |
| 4,018,653 | 4/1977 | Mennen | 195/127 |
| 4,424,279 | 1/1984 | Bohn et al. | 436/534 |

OTHER PUBLICATIONS

Takasaki et al. Amino acid sequences of eight phospholipases A2 from the venom of Australian King Brown Snake, *Pseudechis australis*, Toxicon 28(3): 329–339, 1990.

Kini & Evans. Effects of snake venom proteins on blood platelets. Toxicon 28(12): 1387–1422, 1990.

Kini & Evans. A model to explain the pharmacological effects of snake venom phospholipases A2. Toxicon 27(6): 613–635, 1989.

Chow et al., "Purification, Characterization, and Amino Acid Sequence Determination of Acanthins, Potent Inhibitors of Platelet Aggregation from *Acanthophis antarcticus* (Common Death Adder) Venom," *Archives of Biochemistry and Biophysics*, vol. 354, No. 2, pp. 232–238 (Jun. 15, 1988).

*Primary Examiner*—Karen Cochrane Carlson
*Assistant Examiner*—Holly Schnizer
*Attorney, Agent, or Firm*—Baker Botts LLP

[57] ABSTRACT

The present invention relates generally to protein molecules and to derivatives, homologues, analogues and mimetics thereof capable of inducing or facilitating inhibition of blood clot formation and more particularly platelet aggregation. The present invention also contemplates genetic sequences encoding said protein molecules and derivatives, homologues, analogues and mimetics thereof. The molecules of the present invention are useful inter alia in a range of therapeutic and prophylactic applications.

6 Claims, 5 Drawing Sheets

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Gly Ala Arg Ser Trp Leu Ser Tyr Val Asn
               5                 10

(2) INFORMATION FOR SEQ ID NO:2:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Gly Pro Lys Met Thr Leu Tyr Ser Trp Glu Ala Ala Asn Asp Val
               5                 10               15

Pro Val (2) INFORMATION FOR SEQ ID NO:3:

(i) SEQUENCE CHARACTERISTICS:
      (A) LENGTH: 17 amino acids
      (B) TYPE: amino acid (C) STRANDEDNESS: single
        (D) TOPOLOGY: linear (ii) MOLECULE TYPE: peptide (xi) SEQUENCE DESCRIPTION: SEQ ID NO:3:

Ala Pro Tyr Asn Lys Asn Asn Ile Gly Ile Gly Ser Lys Thr Arg
                  5                  10                  15

Ala Gln (2) INFORMATION FOR SEQ ID NO:4:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Asn Leu Tyr Gln Phe Gly Gly Met Ile Gln Cys Ala Asn Lys Gly
                  5                  10                  15

Ala Arg Ser Trp Leu Ser Tyr Val Asn Tyr Gly Cys Tyr Cys Gly
                 20                  25                  30

Trp Gly Gly Ser Gly Lys Pro Val Asp Glu Leu Asp Arg Cys Cys
                 35                  40                  45

Gln Ile His Asp Asn Cys Tyr Gly Glu Ala Glu Lys Lys Arg Cys
                 50                  55                  60

Gly Pro Lys Met Thr Leu Tyr Ser Trp Glu Cys Ala Asn Asp Val
                 65                  70                  75

Pro Val Cys Asn Ser Lys Ser Ala Cys Glu Gly Phe Val Cys Asp
                 80                  85                  90

Cys Asp Ala Ala Ala Lys Cys Phe Ala Lys Ala Pro Tyr Asn
                 95                 100                 105

Lys Asn Asn Ile Gly Ile Gly Ser Lys Thr Arg Cys Gln
                110                 115

(2) INFORMATION FOR SEQ ID NO:5:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Gly Pro Lys Met Thr Leu Tyr Ser Trp Glu Xaa Ala Asn Asp Val
                  5                  10                  15

Pro Val (2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear -continued

```
    (ii) MOLECULE TYPE: peptide (xi) SEQUENCE DESCRIPTION: SEQ ID NO:6:

Ala Pro Tyr Asn Lys Asn Asn Ile Gly Ile Gly Ser Lys Thr Arg
                  5                  10                  15
Xaa Gln
```

PROTEIN MOLECULES AND USES THEREFOR

FIELD OF THE INVENTION

The present invention relates generally to protein molecules and to derivatives, homologues, analogues and mimetics thereof capable of inducing or facilitating inhibition of blood clot formation and more particularly platelet aggregation. The present invention also contemplates genetic sequences encoding said protein molecules and derivatives, homologues, analogues and mimetics thereof. The molecules of the present invention are useful inter alia in a range of therapeutic and prophylactic applications.

BACKGROUND OF THE INVENTION

Platelets are essential elements involved in haemostatic events. Their role in hemostasis is distinguished by two distinct response: (1) adhesion—the interaction of platelets with subendothelial connective tissue and (2) aggregation—platelet to platelet cohesion. Abnormal platelet function may contribute to a variety of pathophysiological conditions including thrombosis, atherosclerosis, myocardial infarction, stroke and pulmonary embolism.

Inhibitors of platelet aggregation are important in the prevention and treatment of, inter alia, cardiovascular and cerebrovascular diseases. The use of such inhibitors helps in the prevention of unwanted clots which could have detrimental or debilitating effects on patients with high blood pressure, atherosclerosis and other related diseases. These inhibitors are either proteinaceous or non-proteinaceous in nature and inhibit platelet aggregation by a variety of mechanisms. For example, the enzyme inhibitors such as ADPase, fibrinogenase and phospholipase $A_2$ and the non-enzymatic proteins such as disintergrins and mambin exert their inhibitory effect by various mechanisms. These inhibitors exert their antiplatelet actions by various mechanisms. In the case of nonenzymatic proteins the mechanism appears to by simpler. Mambin and disintegrins that contain Arg-Gly-Asp (RGD) sequence exert their action by competively blocking fibrinogen binding to platelet glycoprotein IIb/IIIA. $Ca^{2+}$-dependent type lectin-related proteins exhibit the effects on platelet agglutination and aggregation by specifically binding to platelet glycoprotein Ib. Among enzymes, some proteinases have been studied for their antiplatelet effects. The inhibitory activity of fibrinogenase was initially thought to be due to fibrinogen degradation, since fibrinogen is involved in the final stages of platelet aggregation. Subsequent studies have shown that fibrinogen is involved in the final stages of platelet aggregation. Recent studies have indicated that some of the metalloproteinases inhibit platelet aggregation by cleaving glycoprotein lb which is a receptor for von-Willebrand factor. The ADPase inhibit platelet aggregation by hydrolysis of ADP to form AMP, an inhibitor of platelet aggregation. Thus these enzymes physically destroy either ligand and/or receptor due to their inherent enzymatic activity. Accordingly, different inhibitors have distinct advantages and therefore new sources of anti-clotting agents are constantly sought.

The increasing demand for new pharmaceutical agents has led the pharmaceutical industry to consider molecules found in the natural environment. Accordingly, much effort is being spent on screening aquatic environments, riverbeds, coral, plants, microorganisms and higher animals for potentially useful molecules. The screening process is often referred to as "natural product screening".

In work leading up to the present invention, the inventors have studied snake venom from the common Death Adder (*Acanthophis antarcticus*) and have identified and sequenced a novel protein molecule capable of inhibiting platelet aggregation.

SUMMARY OF THE INVENTION

One aspect of the present invention provides a protein from snake venom or a derivative, homologue, analogue or mimetic thereof which protein is capable of inducing or facilitating the inhibition of blood clotting.

Another aspect of the present invention provides a protein from *Acanthophis antarcticus* venom or a derivative, homologue, analogue or mimetic thereof, which protein is capable of inducing or facilitating the inhibition of blood clotting.

Yet another aspect of the present invention provides a protein comprising an amino acid sequence substantially as set forth in SEQ ID NO:1 or a derivative, homolog, analogue or mimetic thereof or a sequence having at least 50% similarity to SEQ ID NO:1 which protein is capable of inducing or facilitating blood clotting.

A further aspect of the present invention provides a protein comprising an amino acid sequence substantially as set forth in SEQ ID NO:2 or a derivative, homologue, analogue or mimetic thereof or a sequence having at least 50% similarity to SEQ ID NO:2 which protein is capable of inducing or facilitating blood clotting.

Yet another further aspect of the present invention provides a protein comprising an amino acid sequence substantially as set forth in SEQ ID NO:3 or a derivative, homologue, analogue or mimetic thereof or a sequence having at least 50% similarity to SEQ ID NO:3 which protein is capable of inducing or facilitating blood clotting.

Still yet another aspect of, the present invention provides a protein comprising an amino acid sequence substantially as set forth in SEQ ID NO:4 or a derivative, homologue, analogue or mimetic thereof or a sequence having at least 50% similarity to SEQ ID NO:4 which protein is capable of inducing or facilitating blood clotting.

Still yet another further aspect of the present invention provides a protein comprising an amino acid sequence substantially as set forth in SEQ ID NO:4 or a derivative, homologue, analogue or mimetic thereof or a sequence having at least 50% similarity to SEQ ID NO:4.

In yet another aspect of the present invention provides a protein from snake venom having the following characteristics:
  (i) induces or facilitates inhibition of platelet aggregation;
  (ii) its clotting ability is not due to its interaction between fibrinogen and glycoproteinIIb/IIIA-complex;
  (iii) its clotting ability is not due to enzymatic activity or a derivative, homologue, analogue, or mimetic of said protein.

Another aspect of the present invention provides a peptide or a derivative, homologue, analogue or mimetic thereof which comprises an amino acid sequence which is at least 50% similar to a sequence of amino acids in Acanthin and which peptide of capable of inducing or facilitating the inhibition of blood clotting.

Still another aspect of the present invention provides a peptide comprising a sequence of amino acids from about 2 to about 50 residues having at least about 50% similarity to a sequence of amino acids from Acanthin wherein said peptide is capable of inducing or facilitating the inhibition of platelet aggregation or a derivative, homologue, analogue or mimetic of said peptide.

Yet another aspect of the present invention provides a peptide having the following characteristics:

(i) induces or facilitates inhibition of platelet aggregation;

(ii) comprises from about 2 to about 50 amino acid residues;

(iii) its clotting ability is not due to its enzymatic activity or a derivative, homologue, analogue or mimetic of said peptide.

A further aspect of the present invention provides a peptide comprising the amino acid sequence:

G A R S W L S Y V N (SEQ ID NO:1);

or derivatives, homologues, analogues or mimetics thereof.

Another further aspect of the present invention provides a peptide comprising the amino acid sequence:

G P K M T L Y S W E X A N D V P V (SEQ ID NO:5);

wherein X is cysteine or alanine or a derivative, homologue, analogue or mimetic thereof. Preferably, said peptide comprises the amino acid sequence:

G P K M T L Y S W E A A N D V P V (SEQ ID NO:2).

Still yet another further aspect of the present invention provides a peptide comprising the amino acid sequence:

A P Y N K N N I G I G S K T R X Q (SEQ ID NO: 6);

wherein X is cysteine or alanine or a derivative, homologue, analogue or mimetic thereof. Preferably, said peptide comprises the amino acid sequence

A P Y N K N N I G I G S K T R A Q (SEQ ID NO: 3).

The present invention also provides a nucleic acid molecule comprising a sequence of nucleotides encoding or complementary to a sequencing encoding Acanthin as hereinbefore defined or a derivative or homologue thereof.

Another aspect of the present invention provides a nucleic acid molecule which encodes or is complementary to a sequence which encodes an amino acid sequence comprising SEQ ID NO:1 or a derivative, homologue, analogue or mimetic thereof or having at least 50% or greater similarity to SEQ ID NO:1 or a derivative, homologue, analogue or mimetic thereof.

Yet another aspect of the present invention provides a nucleic acid molecule which encodes or is complementary to a sequence which encodes an amino acid sequence comprising SEQ ID NO:2 or a derivative, homologue, analogue or mimetic thereof or having at least 50% or greater similarity to SEQ ID NO:2 or a derivative, homologue, analogue or mimetic thereof.

In yet another aspect the present invention provides a nucleic acid molecule which encodes or is complementary to a sequence which encodes an amino acid sequence comprising SEQ ID NO:3 or a derivative, homologue, analogue or mimetic thereof or having at least 50% of greater similarity to SEQ ID NO:3 or a derivative, homologue, analogue or mimetic thereof.

Still yet another aspect of the present invention provides a nucleic acid molecule which encodes or is complementary to a sequence which encodes an amino acid sequence comprising SEQ ID NO:4 or a derivative, homologue, analogue or mimetic thereof or having at least 50% or greater similarity to SEQ ID NO:4 or a derivative, homologue, analogue or mimetic thereof.

The present invention further provides a nucleic acid molecule comprising a nucleotide sequence encoding or complementary to a sequence encoding an amino acid sequence comprising SEQ ID NO:1 or 2 or 3 or 4 or a derivative, homologue, analogue or mimetic thereof capable of hybridising to said nucleic acid molecule under low stringency conditions at 42° C. and which encodes an amino acid sequence corresponding to an amino acid sequence set forth in SEQ ID NO:1 or 2 or 3 or 4 or a sequence having at least about 50% similarity to SEQ ID NO:1 or 2 or 3 or 4.

The present invention also provides a nucleic acid molecule which encodes or is complementary to a sequence which encodes the peptide:

G A R S W L S Y V N (SEQ ID NO: 1);

or a derivative, homologue, analogue or mimetic thereof.

The present invention still further provides a nucleic acid molecule which encodes or is complementary to a sequence which encodes the peptide:

G P K M T L Y S W E X A N D V P V (SEQ ID NO:5);

wherein X is cysteine or alanine or a derivative, homologue, analogue or mimetic thereof. Preferably said peptide comprises the amino acid sequence

G P K M T L Y S W E A A N D V P V (SEQ ID NO:2).

The present invention yet further provides a nucleic acid molecule which encodes or is complementary to a sequence which encodes the peptide:

A P Y N K N N I G I G S K T R X Q (SEQ ID NO:6);

wherein X is cysteine or alanine or a derivative, homologue, analogue or mimetic thereof. Preferably said peptide comprises the amino acid sequence:

A P Y N K N N I G I G S K T R A Q (SEQ ID NO:3).

Another aspect of the present invention provides the use of Acanthin in the manufacture of a medicament for inducing or facilitating inhibition of platelet aggregation.

Still another aspect of the present invention provides an agent useful for inducing or facilitating inhibition of platelet aggregation comprising Acanthin as hereinbefore defined.

Even yet another aspect of the present invention provides a method of inhibiting platelet aggregation in a subject said method comprising administering to said subject an anti-clottting effective amount of Acanthin hereinbefore defined for a time and under conditions sufficient to inhibit platelet aggregation.

The present invention further provides a composition for use in inhibiting or facilitating inhibition of platelet aggregation comprising Acanthin as hereinbefore defined and one or more pharmaceutically acceptable carriers and/or diluents. The composition may also comprise two different types of proteins such as Acanthin and a known anti-clotting compound or molecule Still another aspect of the present invention is directed to antibodies to Acanthin and their derivatives, homologues, analogues and mimetics. Such antibodies may be monoclonal or polyclonal.

Still yet another aspect of the present invention contemplates a method for detecting Acanthin in a biological sample from a subject or culture supernatant flow or other source said method comprising contacting said biological sample with an antibody specific for Acanthin or its derivative, homologue, analogue or mimetic for a time and under conditions sufficient for an antibody-protein complex to form, and then detecting said complex.

Throughout this specification and claims which follow, unless the context requires otherwise, the word "comprise", or variations such as "comprises" or "comprising", will be understood to imply the inclusion of a stated integer or group of integers but not the exclusion of any other integer or group of integers.

Single and three letter abbreviations used throughout the specification are defined in Table 1.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

DETAILED DESCRIPTION OF THE INVENTION

Figure 1:
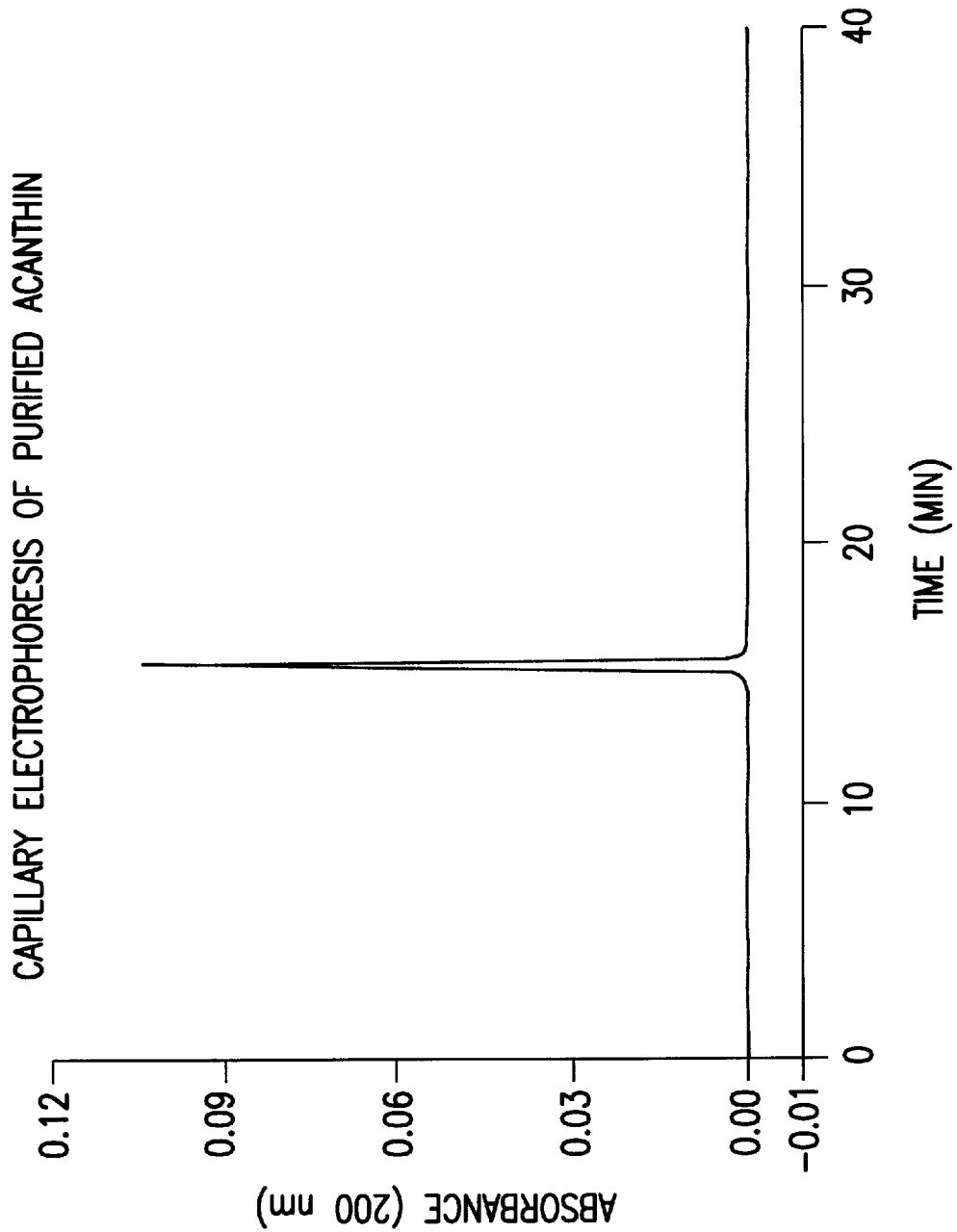
FIG. 1 is a graphical representation of Capillary electrophoresis of purified Acanthin. Conditions: Capillary: 25×24 m, coated; 0.1M phosphate buffer, pH 2.5; injection:pressure loading 5 psi/sec; 4 m/run conditions: 12 kV, constant voltage; detection: UV 200 nm.

The present invention provides a protein from snake venom or a derivative, homologue, analogue or mimetic thereof which protein is capable of inducing or facilitating the inhibition of blood clotting. Said molecule is conveniently in isolated or purified form.

More particularly, the present invention provides a protein from *Acanthophis antarcticus* venom or a derivative, homologue, analogue or mimetic thereof, which protein is capable of inducing or facilitating the inhibition of blood clotting.

In a preferred embodiment the present invention provides a protein comprising an amino acid sequence substantially as set forth in SEQ ID NO:1 or a derivative, homologue, analogue or mimetic thereof or a sequence having at least 50% similarity to SEQ ID NO: 1 which protein is capable of inducing or facilitating blood clotting.

In another preferred embodiment the present invention provides a protein comprising an amino acid sequence substantially as set forth in SEQ ID NO:2 or a derivative, homologue, analogue or mimetic thereof or a sequence having at least 50% similarity to SEQ ID NO:2 which protein is capable of inducing or facilitating blood clotting.

In yet another preferred embodiment the present invention provides a protein comprising an amino acid sequence substantially as set forth in SEQ ID NO:3 or a derivative, homologue, analogue or mimetic thereof or a sequence having at least 50% similarity to SEQ ID NO:3 which protein is capable of inducing or facilitating blood clotting.

Most preferably, the present invention provides a protein comprising an amino acid sequence substantially as set forth in SEQ ID NO:4 or a derivative, homologue, analogue or mimetic thereof or a sequence having at least 50% similarity to SEQ ID NO:4 which protein is capable of inducing or facilitating blood clotting.

The molecule according to this most preferred aspect of the present invention is referred to herein as "Acanthin" and is defined by the amino acid sequence set out in SEQ ID NO:4. Reference hereinafter to Acanthin should be read as including reference to all other snake venom derived proteins or peptides or encoding nucleic acid sequences encompassed by the present invention as well as derivatives, homologues, analogues or mimetics thereof.

Another aspect of the present invention provides a protein comprising an amino acid sequence substantially as set forth in SEQ ID NO:4 or a derivative, homologue, analogue or mimetic thereof or a sequence having at least 50% similarity to SEQ ID NO:4.

The term "similarity" as used herein includes exact identity between compared sequences at the nucleotide or amino acid levels. Where there is non-identity of the nucleotide level "similarity" includes differences between sequences which result in different amino acids that are nevertheless related to each other at the structural, functional, biochemical and/or confirmational levels. Where there is non-identity at the amino acid level, "similarity" includes amino acids that are nevertheless related to each other at the structural, functional, biochemical and/or conformational levels.

The term "blood clotting" is used in its broadest sense to include reference to any one or more steps of the blood clotting cascade such as, but not limited to, platelet aggregation. It should also be understood to refer to the aggregation of any one or more components of the blood such as, but not limited to, platelets. Reference to "inhibition" of said clotting is a reference to complete or partial prevention of blood clot formation. For example, the proteins of the present invention may completely prevent platelet aggregation or they may merely reduce the extent of platelet aggregation. Preferably said blood clotting is platelet aggregation. Reference hereinafter to "platelet aggregation" should be understood as a reference to all forms of blood clotting.

The subject of the platelet aggregation is generally an animal or bird such as but not limited to a human, primate, livestock animal (e.g. sheep, cow, horse, donkey, pig), companion animal (e.g. dog, cat), laboratory test animal (e.g. mouse, rat, guinea pig, rabbit, hamster), captive wild animal (e.g. deer, fox), caged bird (e.g. parrot) and poultry bird (e.g. chicken, duck, pheasant, goose, turkey). Preferably, the subject is a human or primate. Most preferably, the subject is a human.

Reference to a protein capable of "inducing or facilitating" the inhibition of platelet aggregation should be understood as a reference to the inhibition of platelet aggregation by both direct and indirect mechanisms. For example, said protein may interact directly with platelets to prevent their aggregation or, alternatively, may act indirectly to prevent aggregation by, for example, inhibiting one or more of the biological signals which result in the induction of platelet aggregation.

The term "protein" should be understood to encompass polypeptides and proteins. The protein may be glycosylated or unglycosylated and/or may contain a range of other molecules fused, linked, bound or otherwise associated to the protein such as amino acids, lipids, carbohydrates or other peptides, polypeptides or proteins. Reference hereinafter to a "protein" includes a protein comprising a sequence of amino acids as well as a protein associated with other molecules such as amino acids, lipids, carbohydrates or other polypeptides or proteins.

Without limiting the present invention to any one theory or mode of action, Acanthin exhibits the enzymatic activity of phospholipase $A_2$. However, modifying the active site histidine residue to reduce by greater than 98% the enzymatic activity of Acanthin reveals that phospholipid hydrolysis does not contribute to the inhibition of platelet aggregation. Further, unlike other known inhibitors, Acanthin does not induce platelet aggregation via an interaction between fibrinogen and its receptor, glycoprotein IIb-IIIA complex, thereby minimizing the possibility of Acanthin interfering with other adhesion reaction.

Accordingly, in another aspect the present invention provides a protein from snake venom having the following characteristics.

(i) induces or facilitates inhibition of platelet aggregation;

(ii) its clotting ability is not due to its interaction between fibrinogen and glycoprotein IIb/IIIA-complex;

(iii) its clotting ability is not due to enzymatic activity or a derivative, homologue, analogue, or mimetic of said protein.

Preferably, said protein comprises an amino acid sequence substantially as set forth in SEQ ID NO:1.

In another preferred embodiment said protein comprises an amino acid sequence substantially as set forth in SEQ ID NO:2.

In yet another preferred embodiment said protein comprises an amino acid sequence substantially as set forth in SEQ ID NO:3.

In still yet another most preferred embodiment said protein comprises an amino acid sequence substantially as set forth in SEQ ID NO:4.

Based on the structural comparisons of Acanthin with sequences of phospholipase A, enzymes derived from Australian snake venoms, and using proline bracket theory the inventors have predicted three amino acid sequence segments which act as interaction sites.

Accordingly, another aspect of the present invention provides a peptide or a derivative, homologue, analogue or mimetic thereof which comprises an amino acid sequence which is at least 50% similar to a sequence of amino acids in Acanthin and which peptide is capable of inducing or facilitating the inhibition of blood clotting.

Preferably, said blood clotting is platelet aggregation.

The term "peptide" encompasses a proteinaceous molecule comprising from about 2 amino acid residues to about 50 amino acid residues. Preferably, the peptide comprises from about 3 amino acid residues to about 40 amino acid residues. Even more preferably, the peptide comprises from about 4 amino acid residues to about 30 amino acid residues. Particularly preferred embodiments include peptides comprising from about 4 amino acid residues to about 20 amino acid residues such as from 4 to 10, 4 to 16, and 4 to 17 amino acid residues.

The peptide may be glycosylated or unglycosylated and/ or may contain a range of other molecules fused, linked, bound or otherwise associated to the peptide such as amino acids, lipids, carbohydrates or other peptides, polypeptides or proteins. Reference herein after to a "peptide" includes a peptide comprising a sequence of amino acids as well as a peptide associated with other molecules such as amino acids, lipids, carbohydrates or other peptides, polypeptides or proteins.

In a particularly preferred embodiment, there is provided a peptide comprising a sequence of amino acids from about 2 to about 50 residues having at least about 50% similarity to a sequence of amino acids from Acanthin wherein said peptide is capable of inducing or facilitating the inhibition of platelet aggregation or a derivative, homologue, analogue or mimetic of said peptide.

The percentage similarity may be greater than 60% such as at least 70% or at least 80% or at least 90% or higher.

Another preferred embodiment of the present invention provides a peptide having the following characteristics:

(i) induces or facilitates inhibition of platelet aggregation;

(ii) comprises from about 2 to about 50 amino acid residues;

(iii) its clotting ability is not due to its enzymatic activity or a derivative, homologue, analogue or mimetic of said peptide.

A particularly preferred peptide of the present invention comprises the amino acid sequence:

G A R S W L S Y V N (SEQ ID NO: 1);

or derivatives, homologues, analogues or mimetics thereof.

Another particularly preferred peptide of the present invention comprises the amino acid sequence:

G P K M T L Y S W E X A N D V P V (SEQ ID NO:5);

wherein X is cysteine or alanine or a derivative, homologue, analogue or mimetic thereof. Preferably, said peptide comprises the amino acid sequence:

G P K M T L Y S W E A A N D V P V (SEQ ID NO:2).

Yet another particularly preferred peptide of the present invention comprises the amino acid sequence:

A P Y N K N N I G I G S K T R X Q (SEQ ID NO: 6);

wherein X is cysteine or alanine or a derivative, homologue, analogue or mimetic thereof. Preferably, said peptide comprises the amino acid sequence:

A P Y N K N N I G I G S K T R A Q (SEQ ID NO: 3).

The proteins and peptides of the present invention may be produced by chemical synthetic techniques or may be produced by recombinant DNA technology as discussed further below. The peptides may also be fragments of larger molecules from snake venom. The fragments may be naturally occurring fragments or generated by the action of proteases, petidases, amidases, lysins or other enzymes as well as by sonic disruption, heat, chemical disruption and/or shearing.

Reference herein to "derivatives" includes parts, fragments and portions of Acanthin. A derivative also includes a single or multiple amino acid substitution, deletion and/or addition. Homologues include functionally, structurally or stereochemically similar peptides from venom from the same species of snake or from within the genus or family of snakes or from any other reptilian or non-reptilian species.

Preferred snakes include snakes from the family Colubridae, Elapidae, Viperidae and Crotalidae such as species of the genera Naja, Dendroaspis, Bungarus, Pseudechis, Ophiophagus and Hemachatus. Particularly preferred snakes are from the family Elapidae such as but not limited to King cobra (*Ophiohagus hannah*), True cobras (Naja spp); Asian or Indian cobra (*N. naja*); Egyptian cobra (*N. haje*), Spitting cobra (*N. nigeicollis*); Black-lipped cobra (*N. melanoleuca*); Cape cobra (*N. nivea*); Gold's tree cobra (*Pseudohaje goldii*); Desert black snakes (Walterinnesia spp); Shield-nose snakes (Aspidelaps spp); Water cobras or water snakes (Boulengerina spp); Black mamba (*Dendroaspis polylepis*); Mamba (*D. angusticeps*); Kraits snake (Bungarus spp); Oriental coral snakes (Calliophis spp); Long-glanded coral snakes (Maticora spp); American coral snakes (Micurus spp); Southern coral snake (*M. frontalis*); Eastern coral snake or Harlequin snake (*M. fulvius*); Western coral snake (Micruroides spp); Arizona coral snake (*M. euryxanthus*); Death adder (*Acanthophis antarcticus*); Australian tiger snakes (Notechis spp); and Australian copperhead (Denisomia spp).

Analogues and mimetics include molecules which contain non-naturally occurring amino acids or which do not contain amino acids but nevertheless behave functionally the same as the protein. Natural product screening is one useful strategy for identifying analogues and mimetics. Analogues of Acanthin contemplated herein include modifications to side chains, incorporation of unnatural amino acids and/or their derivatives during peptide synthesis and the use of crosslinkers and other methods which impose conformational constraints on the protein molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is shown in Table 2.

TABLE 2

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |

TABLE 2-continued

| Non-conventional amino acid | Code | Non-conventional amino acid | Code |
| --- | --- | --- | --- |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-a-methylornithine | Morn |
| L-α-methylphenylalanine | Mphe | L-a-methylproline | Mpro |
| L-α-methylserine | Mser | L-a-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates chemical analogues of Acanthin capable of acting as antagonists or agonists of said protein. Chemical analogues may not necessarily be derived from Acanthin itself but may share certain conformational similarities. Alternatively, chemical analogues may be specifically designed to mimic certain physiochemical properties of Acanthin. Chemical analogues may be chemically synthesised or may be detected following, for example, natural product screening.

All these types of modifications may be important to stabilise Acanthin if administered to a subject.

The present invention further contemplates recombinant inhibitory proteins and peptides.

Accordingly, another aspect of the present invention provides a nucleic acid molecule comprising a sequence of nucleotides encoding or complementary to a sequencing encoding Acanthin as hereinbefore defined or a derivative, homologue, analogue or mimetic thereof.

A particularly useful nucleic acid molecule is one which encodes or is complementary to a sequence which encodes an amino acid sequence comprising SEQ ID NO:1 or a derivative, homologue, analogue or mimetic thereof or having at least 50% or greater similarity to SEQ ID NO:1 or a derivative, homologue, analogue or mimetic thereof.

Another particularly useful nucleic acid molecule is one which encodes or is complementary to a sequence which encodes an amino acid sequence comprising SEQ ID NO:2 or a derivative, homologue, analogue or mimetic thereof or having at least 50% or greater similarity to SEQ ID NO:2 or a derivative, homologue, analogue or mimetic thereof.

Yet another particularly useful nucleic acid molecule is one which encodes or is complementary to a sequence which encodes an amino acid sequence comprising SEQ ID NO:3 or a derivative, homologue, analogue or mimetic thereof or having at least 50% of greater similarity to SEQ ID NO:3 or a derivative, homologue, analogue or mimetic thereof.

A most preferable nucleic acid molecule is one which encodes or is complementary to a sequence which encodes an amino acid sequence comprising SEQ ID NO:4 or a derivative, homologue, analogue or mimetic thereof or having at least 50% or greater similarity to SEQ ID NO:4 or a derivative, homologue, analogue or mimetic thereof.

Another aspect of the present invention provides a nucleic acid molecule comprising a nucleotide sequence encoding or complementary to a sequence encoding an amino acid sequence comprising SEQ ID NO:1 or 2 or 3 or 4 or a derivative, homologue, analogue or mimetic thereof capable of hybridising to said nucleic acid molecule under low stringency conditions at 42°0 C. and which encodes an amino acid sequence corresponding to an amino acid sequence set forth in SEQ ID NO:1 or 2 or 3 or 4 or a sequence having at least about 50% similarity to SEQ ID NO:1 or 2 or 3 or 4.

A particularly useful nucleic acid molecule is one which encodes or is complementary to a sequence which encodes the peptide:

G A R S W L S Y V N (SEQ ID NO: 1);

or a derivative, homologue, analogue or mimetic thereof.

Another particularly useful nucleic acid molecule is one which encodes or is complementary to a sequence which encodes the peptide:

G P K M T L Y S W E X A N D V P V (SEQ ID NO:5);

wherein X is cysteine or alanine or a derivative, homologue, analogue or mimetic thereof. Preferably said peptide comprises the amino acid sequence

G P K M T L Y S W E A A N D V P V (SEQ ID NO:2).

Yet another particularly useful nucleic acid molecule is one which encodes or is complementary to a sequence which encodes the peptide:

A P Y N K N N I G I G S K T R X Q (SEQ ID NO:6);

wherein X is cysteine or alanine or a derivative, homologue, analogue or mimetic thereof. Preferably said peptide comprises the amino acid sequence

A P Y N K N N I G I G S K T R A Q (SEQ ID NO: 3).

The nucleic acid molecule of the present invention is generally in isolated form. It may also comprise additional nucleotide sequence information fused, linked or otherwise associated with it either at the 3' or 5' terminal portions or at both the 3' and 5' terminal portions. The nucleic acid molecule may also be part of a vector, such as an expression vector. The latter embodiment facilitates production of recombinant forms of Acanthin which forms are encompassed by the present invention.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

The present invention further encompasses host cells for the subject nucleic acid molecules and which are used to produce recombinant Acanthin. The host cells may be prokaryotic cells or eukaryotic cells. Examples of prokaryotic cells include *E. coli*, Bacillus sp, Pseudomonas sp amongst many others. Examples of eukaryotic cells include mammalian cell lines (eg. CHO cells), yeast cells, fungal cells, insect cells, plant cells and reptilian cell lines. The ability to produce recombinant Acanthin of the present invention permits the large scale production of vast qualities of Acanthin for commercial uses. As stated above, the Acanthin may need to be produced as part of a large peptide, polypeptide or protein which may be used as is or may first need to be processed in order to remove the extraneous proteinaceous sequences. Such processing includes digestion with proteases, peptidases and amidases or a range of chemical, electrochemical, sonic or mechanical disruption techniques.

Notwithstanding that the present invention encompasses recombinant proteins and peptides, chemically synthetic techniques are particularly preferred in the synthesis of Acanthin.

Acanthin according to the present invention is conveniently synthesized based on molecules isolated from snake venom. Isolation of the venom molecules may be accomplished by any suitable means such as by chromatographic separation, for example using CM-cellulose ion exchange chromatography followed by Sephadex (eg. G-50 column) filtration. Many other techniques are available including HPLC, PAGE amongst others. Once purified, the venom derived molecule can be partially sequenced and/or fragments produced and used directly as a source of Acanthin or as a template for amino acid synthesis.

Acanthin may be synthesized by solid phase synthesis using F-moc chemistry as described by Carpino et al (1991). Acanthin and fragments thereof may also be synthesized by alternative chemistries including, but not limited to, t-Boc chemistry as described in Stewart et al (1985) or by either classical methods of liquid phase peptide synthesis.

The present invention further extends to the use of Acanthin in the manufacture of a medicament for inducing or facilitating inhibition of platelet aggregation.

Yet another aspect of the present invention provides an agent useful for inducing or facilitating inhibition of platelet aggregation comprising Acanthin as hereinbefore defined.

As stated above the Acanthin of the present invention is useful in preventing platelet aggregation in a subject such as a mammal (e.g. a human).

Accordingly, another aspect of the present invention contemplates a method of inhibiting platelet aggregation in a subject said method comprising administering to said subject an anti-aggregation effective amount of Acanthin hereinbefore defined for a time and under conditions sufficient to inhibit platelet aggregation.

In accordance with this method, more than one type of protein or peptide may be administered for e.g. the Acanthin may be coadministered with a known anti-clotting compound or molecule. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of proteins or the protein and the known anti-clotting compound or molecule. The Acanthin or the Acanthin and known anti-clotting compound or molecule may be administered in any order.

Routes of administration include but are not limited to intravenously, intraperitoneal, subcutaneously, intracranial, intradermal, intramuscular, intraocular, intrathecal, intracerebrally, intranasally, infusion, orally, rectally, via iv drip, patch and implant. Intravenous routes are particularly preferred.

Another aspect of the present invention provides a composition for use in inhibiting or facilitating inhibition of platelet aggregation comprising Acanthin as hereinbefore defined and one or more pharmaceutically acceptable carriers and/or diluents. The composition may also comprise two different types of proteins or peptides such as Acanthin and a known anti-clotting compound or molecule.

Compositions suitable for injectable use include sterile aqueous solutions (where water soluble) and sterile powders for the extemporaneous preparation of sterile injectable solutions. They must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof and vegetable oils. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by, for example, filter sterilization or sterilization by other appropriate means. Dispersions are also contemplated and these may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

When the active ingredients are suitably protected, they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ng and 2000 mg of active compound.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels. In such forms, the anti-clotting proteins may need to be modified to permit penetration of the surface barrier.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding such an active material for inducing or facilitating inhibition of blood clotting in living subjects.

Effective amounts of anti-clotting proteins contemplated by the present invention will vary depending on the severity of the pain and the health and age of the recipient. In general terms, effective amounts may vary from 0.01 ng/kg body weight to about 100 mg/kg body weight. Alternative amounts include for about 0.1 ng/kg body weight about 100 mg/kg body weight or from 1.0 ng/kg body weight to about 80 mg/kg body weight.

Still another aspect of the present invention is directed to antibodies to Acanthin and their derivatives, homologues, analogues and mimetics. Such antibodies may be monoclonal or polyclonal.

In the case of small peptides, these may first need to be associated with a carrier molecule.

The antibodies of the present invention are particularly useful as therapeutic or diagnostic agents. For example, specific antibodies can be used to screen for Acanthin using immunoassays or used as antagonists to inhibit Acanthin activity under certain circumstances such as where temporary clotting inhibition is only required. Techniques for such immunoassays are well known in the art and include, for example, sandwich assays and ELISA. Knowledge of Acanthin levels may be important for monitoring certain therapeutic protocols.

Antibodies to the Acanthin (or its derivatives, homologues, analogues or mimetics) of the present invention may be monoclonal or polyclonal. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies.

As stated above, specific antibodies can be used to screen for the Acanthin. The latter would be important, for example, as a means for screening for levels of Acanthin in a cell extract or other biological fluid or purifying Acanthin made by recombinant means from culture supernatant fluid.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of Acanthin.

Both polyclonal and monoclonal antibodies are obtainable by immunization with Acanthin and either type is utilizable for immunoassays. The methods of obtaining both types of sera are well known in the art. Polyclonal sera are less preferred but are relatively easily prepared by injection of a suitable laboratory animal with an effective amount of Acanthin, or antigenic parts thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting Acanthin in a biological sample from a subject or culture supernatant flow or other source said method comprising contacting said biological sample with an antibody specific for Acanthin or its derivative, homologue, analogue or mimetic for a time and under conditions sufficient for an antibody-protein complex to form, and then detecting said complex.

The presence of Acanthin may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain a peptide which inhibits blood clotting including cell extract, culture supernatant tissue biopsy, serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the protein or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes or overnight if more convenient) and under suitable conditions (e.g. from room temperature to about 37° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or pcriodate. As will be readily recognized, however, a wide variety of different conjugation techniques exist, which are readily available to the skilled artisan. Commonly used enzymes include horseradish peroxidase, luciferase glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates noted above. In all cases, the enzyme-labelled antibody is added to the first antibody-peptide complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention is further described by the following nonlimiting examples.

EXAMPLE 1

Purification and Sequencing of Acanthin from Venom

Figure 2:
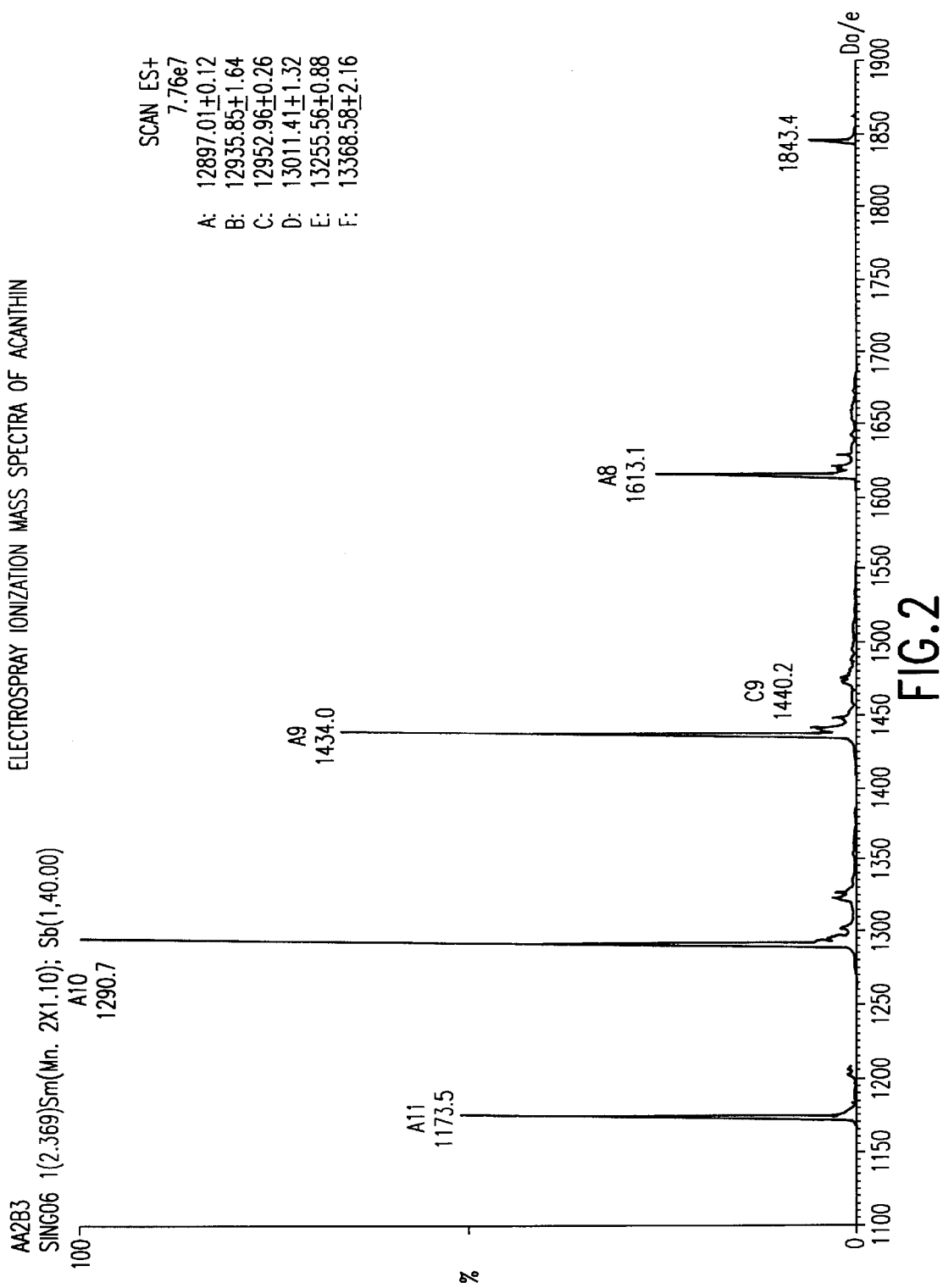
FIG. 2 is a graphical representation of Electrospray ionization mass spectra of Acanthin.

The inventors used a three-step chromatographic method to purify the antiplatelet protein from *Acanthophis antarcticus* venom. The steps included gel filtration on Bio-Gel P-30 column, cation exchange chromatography on a Poros HS column and reversed-phase chromatography on a Ashahipak ODP 50 column. The protein was adjudged homogeneous based on capillary electrophoresis and electrospray ionization mass spectrometry (FIGS. 1 and 2). This protein was named acanthin. The same protein can be purified by alternative methods using either different strategies or alternative columns which are available. This protein can also be produced by recombinant technology.

The amino acid sequence of Acanthin was determined by Edman degradation of native and pyridythylated protein and the peptides generated from the protein.

EXAMPLE 2

Peptide Identification

Based on the structural comparisons with sequences of other phospholyypase $A_2$ enzymes from Australian snake venoms and using proline bracket theory, peptide sequences were predicted as potential interaction sites. These peptides were synthesized and tested for their anti-platelet effects.

EXAMPLE 3

Peptide Functional Assays

Anti-platelet aggregation was tested in an assay which measured inhibition of platelet aggregation, in whole human blood, and induced by collagen. Peptide activity was also measured in whole human blood assays in which aggregation was induced by ADP.

Binding competition between peptide and protein is examined in addition to the structure-activity relationships of active peptides.

EXAMPLE 4

Inhibition Of Platelet Aggregation

Figure 3:
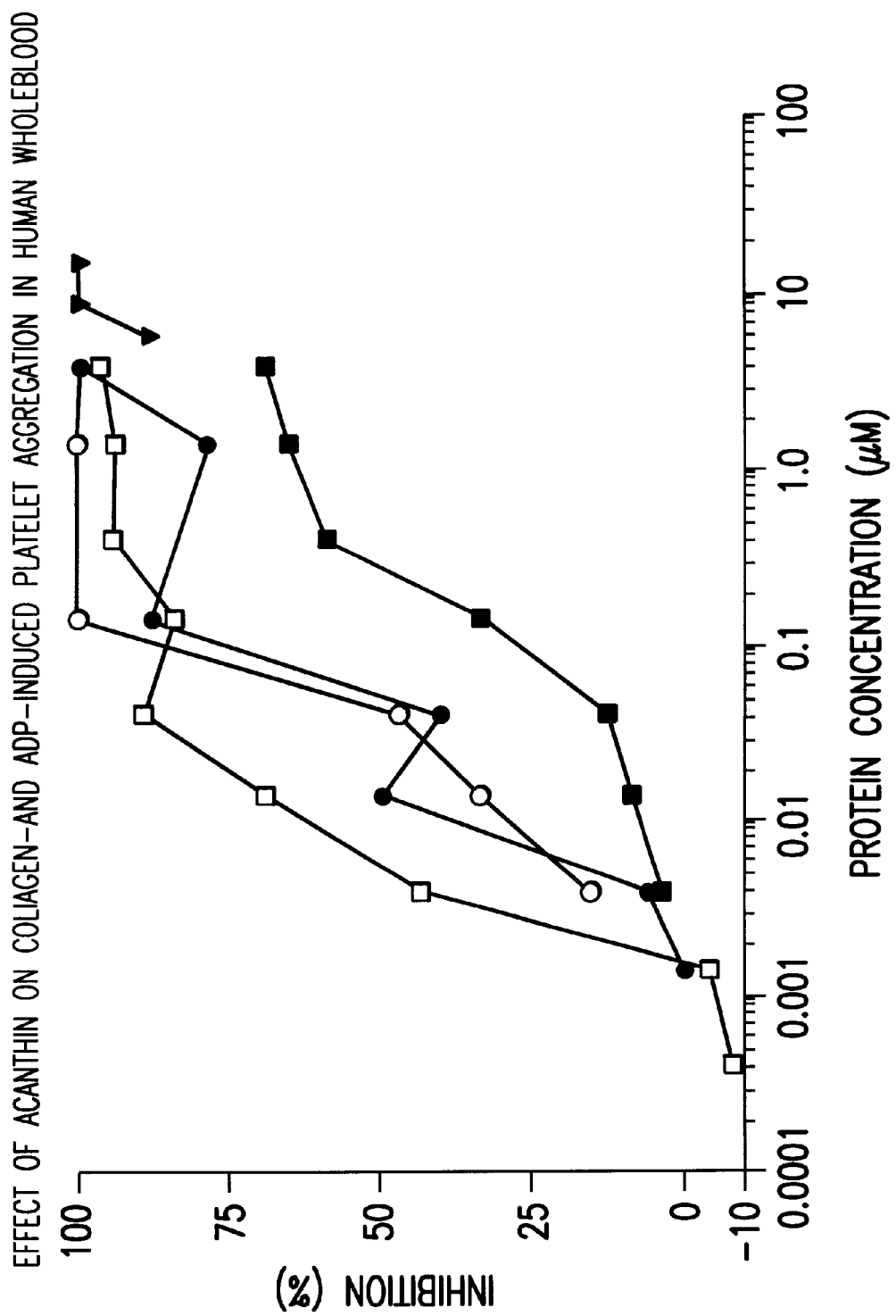
FIG. 3 is a graphical representation of the effect of Acanthin on collagen- and ADP-induced platelet aggregation in human whole blood. Each point represents the average of three measurements standard deviation. Square symbols show the effect of Acanthin on wholeblood aggregation measured using electrical impedance. Open square, ADP-induced; Filled square, collagen-induced. Hexagon symbols show the effect of collagen-induced aggregation of human platelet-rich plasma. Open hexagon, measured by electrical impedance; Filled hexagon, measured by turbodometric method. Filed triangle, ADP-induced aggregation of platelet-rich plasma measured by impedance method.

The protein Acanthin inhibits platelet aggregation in a dose-dependent manner (FIG. 3). The $IC_5 1$ values (concentration of the inhibitor required to inhibit 50% of aggregation) of ADP- and collagen-induced platelet aggregation in human whole blood are 7 nM and 4nM, respectively. Thus acanthin is one of the most potent inhibitors of platelet aggregation.

EXAMPLE 5

Effect of Acanthin Enzymatic Activity on Its Anti-Clotting Properties

Figure 4:
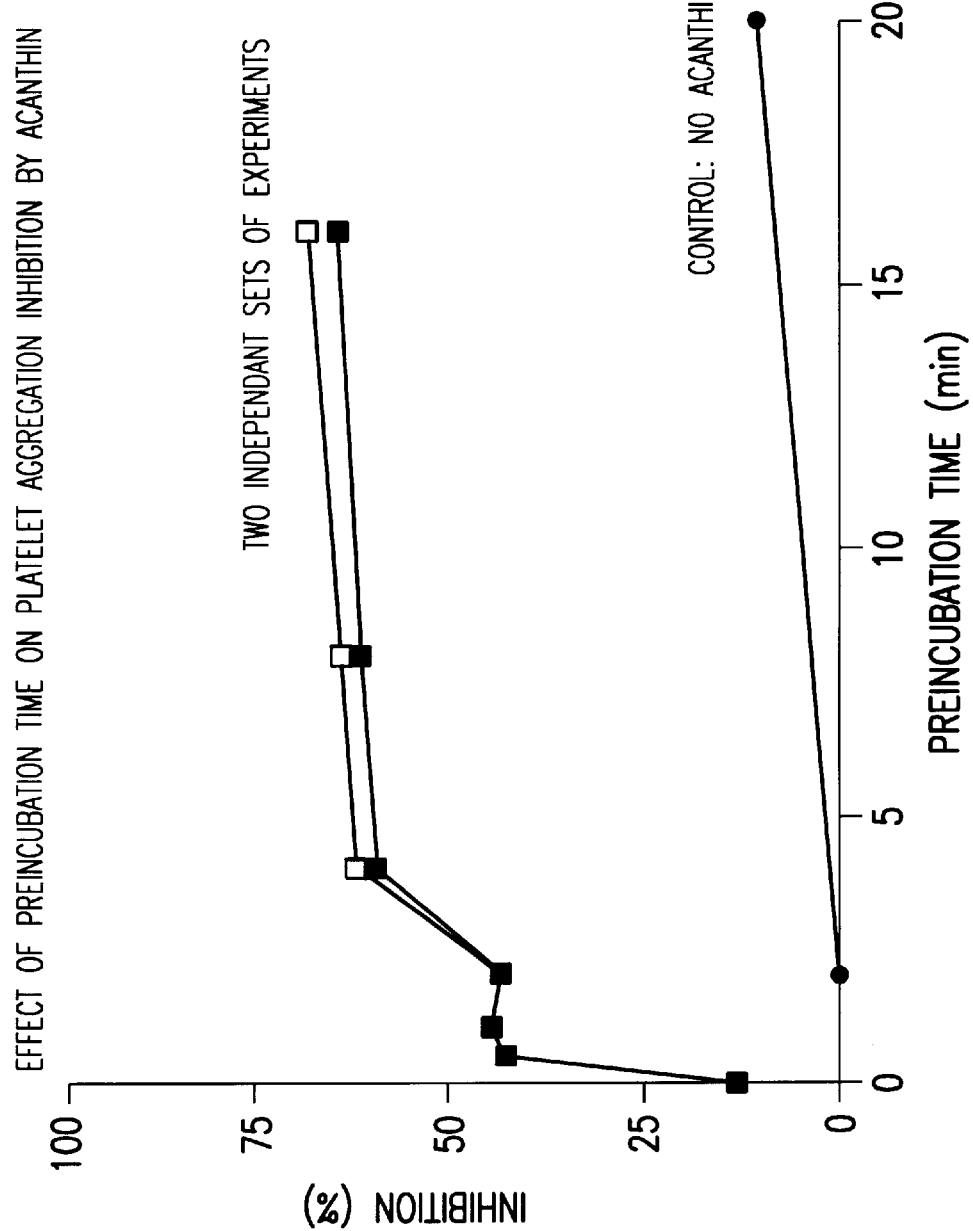
FIG. 4 is a graphical representation of the effect of preincubation time on platelet aggregation inhibition by Acanthin. Filled circle, control; solid and open squares, two independent sets of experiments.
Figure 5:
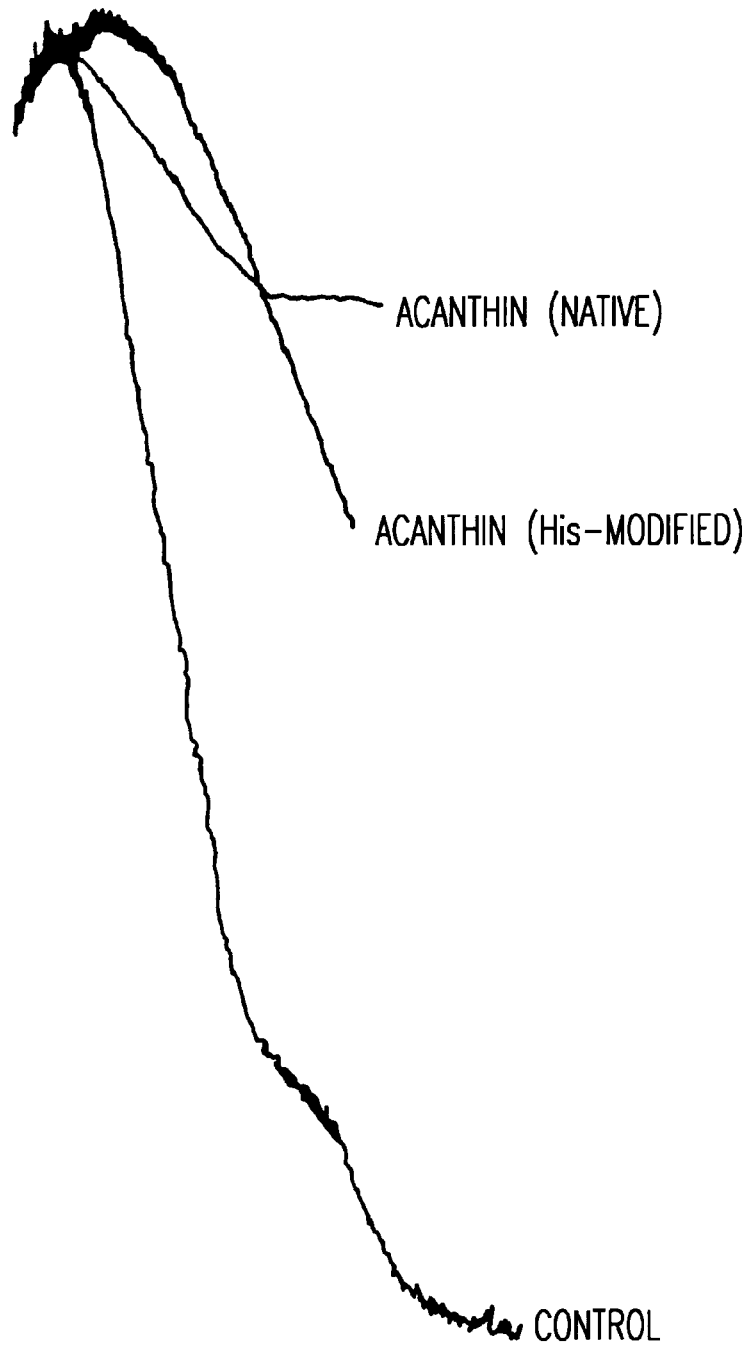
FIG. 5 is a schematic representation of the effect of alkylation of histidine on the antiplatelet effects.

Acanthin exhibits phospholipase $A_2$ activity. Increasing the times of incubation of acanthin with the platelets does not increase the potency of inhibition (FIG. 4). Longer incubation times should result in increased hydrolysis of phospholipids or increased accumulation of hydrolysis products. If phospholipid hydrolysis is important for the anti-platelet activity, then there will be an increase in the anti-platelet effects when the incubation times are increased. Results shown in FIG. 4 indicates that phospholipid hydrolysis does not contribute to the inhibition of platelet aggregation. To further support this, the inventors modified the active site Histidine residue by p-bromophenacylbromide and tested the modified acanthin for its enzymatic and antiplatelet effects. Histidine-alkylated protein lost more than 98% of its enzymatic activity, but it retains significant amounts of its inhibitory effect on platelet aggregation (FIG. 5).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

We claim:

1. An isolated peptide or protein comprising an amino acid sequence selected from the group consisting of SEQ ID NOs: 1, 2, 3, 4, 5, 6 wherein said peptide or protein is capable of inducing or facilitating the inhibition of blood clotting.

2. An isolated protein having the amino acid sequence of SEQ ID NO: 4.

3. An isolated peptide or protein having the amino acid sequence of SEQ ID NO: 4 or a fragment thereof capable of inducing or facilitating the inhibition of blood clotting.

4. An isolated peptide or protein comprising an amino acid sequence selected from the group consisting of SEQ ID NOs: 1, 2, 3, 4, 5, 6 and sequences having at least 90% similarity thereto, wherein said peptide or protein is capable of inducing or facilitating the inhibition of blood clotting.

5. An isolated protein having the amino acid sequence of SEQ ID NO: 4 or a sequence having at least 90% similarity thereto, wherein said protein is capable of inducing or facilitating the inhibition of blood clotting.

6. A composition comprising the isolated peptide of any one of claims 1–5.

* * * * *